(12) United States Patent
Schwenn et al.

(10) Patent No.: US 6,676,620 B2
(45) Date of Patent: Jan. 13, 2004

(54) MODULAR ORTHOSIS CLOSURE SYSTEM AND METHOD

(75) Inventors: Shannon R. Schwenn, Deltona, FL (US); Robert B. Hamilton, III, Orlando, FL (US); John N. Penn, Orlando, FL (US)

(73) Assignee: Orthomerica Products, Inc., Newport Beach, CA (US)

( * ) Notice: Subject to any disclaimer, the term of this patent is extended or adjusted under 35 U.S.C. 154(b) by 251 days.

(21) Appl. No.: 09/730,362

(22) Filed: Dec. 5, 2000

(65) Prior Publication Data

US 2002/0068890 A1 Jun. 6, 2002

(51) Int. Cl.[7] .................................................. A61F 5/00
(52) U.S. Cl. ........................... 602/12; 602/19; 128/96.1
(58) Field of Search ................................ 602/5, 19, 12; 128/95.1, 96.1, 98.1, 99.1, 100.1, 101.1, 105.1–107.1; 2/44–45, 92, 311; 24/713.4, 713.5, 714.6, 715, 715.1, 715.2

(56) References Cited

U.S. PATENT DOCUMENTS

| | | | |
|---|---|---|---|
| 61,487 A | * | 1/1867 | Vollschwitz ................. 24/713 |
| 181,948 A | * | 9/1876 | Kleinschuster ............. 24/714.6 |
| 232,420 A | | 9/1880 | Smith |
| 321,145 A | | 6/1885 | Spencer |
| 321,146 A | | 6/1885 | Spencer |
| 328,638 A | | 10/1885 | Battershall |
| 386,642 A | | 7/1888 | Mann |
| 571,749 A | | 11/1896 | Colton |
| 601,446 A | | 3/1898 | Mestler |
| 629,900 A | | 8/1899 | Fosburgh |
| 746,563 A | | 12/1903 | McMahon |
| 772,926 A | | 10/1904 | Colton |
| 787,894 A | | 4/1905 | McMahon |
| 894,066 A | | 7/1908 | Scarpa |
| 1,060,422 A | | 4/1913 | Bowdish |
| 1,393,188 A | | 10/1921 | Whiteman |
| 1,463,579 A | | 7/1923 | Funck |
| 1,469,661 A | | 10/1923 | Migita |

(List continued on next page.)

OTHER PUBLICATIONS

Brochure: CYBERTECH 2000, Chairback, The Rigid Mechanical Advantage Orthoses, 1998.
Brochure: CYBERTECH 2000, Body Jacket, The Rigid Mechanical Advantage Orthoses, 1998.
Brochure: CYBERTECH 2000, Cruiciform Anterior Spinal Hyperextension, The Rigid Mechanical Advantage Orthoses, 1998.
Brochure: CYBERTECH 2000, TLSO, The Rigid Mechanical Advantage Orthoses, 1998.
Brochure: CYBERTECH 500, New LSO, The Mechanical Advantage Orthoses, 1998.
Brochure: CYBERTECH 1000, The Mechanical Advantage Orthoses, 1998.
Brochure: Orthomerica Products, Inc., Lite Torso Spinal System, 1995.

*Primary Examiner*—Nicholas D. Lucchesi
*Assistant Examiner*—Victor Hwang (57) ABSTRACT

An orthosis can comprise a first body member that can conform to a portion of a patient's body and a second body member that can conform to another portion of a patient's body. A closure unit having a first connector member with a first plurality of support posts can be operatively connected to the first body member, while a second connector member with a second plurality of support posts can be operatively connected to the second body member. An elongated flexible pull member can operatively extend between the respective first and second support posts so that when tightened by a patient, a pull member slides across the support posts to provide a mechanical force advantage to draw the first body member and the second body member against the patient's torso. A closure unit can be of a modular configuration for subjective mounting on various components of an orthosis to provide a highly adaptable closure unit.

24 Claims, 7 Drawing Sheets

U.S. PATENT DOCUMENTS

| | | | | |
|---|---|---|---|---|
| 1,481,903 | A | 1/1924 | Hart | |
| 1,530,713 | A | 3/1925 | Clark | |
| 1,558,661 | A | 10/1925 | Yeganian | |
| 2,036,484 | A | 4/1936 | Le May | |
| 2,100,964 | A | 11/1937 | Kendrick | |
| 2,117,309 | A | 5/1938 | Fritsch | |
| 2,219,475 | A | 10/1940 | Flaherty | |
| 2,409,381 | A | 10/1946 | Pease, Jr. | |
| 2,554,337 | A | 5/1951 | Lampert | |
| 2,749,550 | A | 6/1956 | Pease | |
| 3,371,351 | A * | 3/1968 | Allain | 2/338 |
| 3,834,048 | A | 9/1974 | Maurer | |
| 3,927,665 | A | 12/1975 | Wax | |
| 4,099,524 | A | 7/1978 | Cueman et al. | |
| 4,175,553 | A * | 11/1979 | Rosenberg | 602/19 |
| 4,475,543 | A | 10/1984 | Brooks et al. | |
| 4,508,110 | A | 4/1985 | Modglin | |
| 4,574,789 | A | 3/1986 | Forster | |
| 4,658,807 | A * | 4/1987 | Swain | 602/19 |
| 4,696,291 | A | 9/1987 | Tyo | |
| 4,862,878 | A | 9/1989 | Davison et al. | |
| 4,870,761 | A * | 10/1989 | Tracy | 36/51 |
| 4,937,952 | A | 7/1990 | Olivieri | |
| 5,072,725 | A | 12/1991 | Miller | |
| 5,074,288 | A | 12/1991 | Miller | |
| 5,226,874 | A | 7/1993 | Heinz et al. | |
| 5,259,831 | A | 11/1993 | LeBron | |
| 5,346,461 | A | 9/1994 | Heinz et al. | |
| 5,399,151 | A | 3/1995 | Sjoerdsma et al. | |
| 5,437,617 | A | 8/1995 | Heinz et al. | |
| 5,484,395 | A | 1/1996 | DeRoche | |
| 5,499,965 | A | 3/1996 | Sanchez | |
| 5,599,287 | A | 2/1997 | Beczak, Sr. et al. | |
| 5,634,891 | A | 6/1997 | Beczak, Sr. et al. | |
| 5,853,378 | A | 12/1998 | Modglin | |
| 5,857,988 | A | 1/1999 | Shirley | |
| 5,967,998 | A | 10/1999 | Modglin | |
| 6,110,138 | A | 8/2000 | Shirley | |
| 6,190,343 | B1 * | 2/2001 | Heinz et al. | 602/19 |
| 6,213,968 | B1 * | 4/2001 | Heinz et al. | 602/19 |
| 6,322,529 | B1 * | 11/2001 | Chung | 602/19 |
| 6,517,502 | B2 * | 2/2003 | Heyman et al. | 602/5 |
| 2002/0148461 | A1 * | 10/2002 | Heinz et al. | 128/96.1 |

\* cited by examiner

MODULAR ORTHOSIS CLOSURE SYSTEM AND METHOD

BACKGROUND OF THE INVENTION

1. Field of the Invention

The present invention is directed to a closure system for orthoses which can be manufactured in pre-fabricated modules with an improved pull system to provide a mechanical advantage for applying compression forces to a patient and a method of manufacturing a closure system.

2. Description of the Related Art

Various types of orthotic systems have been suggested to address both injury and degenerate conditions that may occur—for example, a spinal orthosis to effectively stabilize the lumbo-sacral spine. Geriatric patients frequently experience chronic low back pain as a result of vertebral degeneration, discogenic disease and postural deterioration. Orthoses have been proposed to address stabilization of the lumbo-sacral spine and to assist in both pelvic tilt and rotational control. Such orthoses assist the patient in standing, sitting and prone positions by relieving postural stress pain. Various forms of back braces and corsets, both of a flexible and rigid configuration have been proposed, such as U.S. Pat. Nos. 5,072,725, 5,074,288, 4,508,110, 3,927,665, 4,099,524, 4,475,543 and 5,634,9891. Frequently, patients with arthritic hands lack the dexterity to tighten and adjust such lumbo-sacral supports and other types of orthoses. Various forms of hook and pile or nap straps and closure systems, including hook and eye closure systems with buckles, are frequently utilized. Conventional corsets with lacing that is respectively looped through eyelets have provided a mechanical advantage when the lacing is tightened for patients. However, friction can be a factor between the lacing and the eyelets.

Other examples of lumbo-sacral orthoses can be found in U.S. Pat. No. 5,853,378 and U.S. Pat. No. 5,437,617. In each of these patents, a mechanical advantage is secured by either pulling straps through a conventional buckle system on the '378 patent, or by using a series of pulleys in the '617 patent that can be tightened by a motor.

There is a still a demand for relatively economical modular orthoses that can be conveniently used by a patient for a mechanical advantage in exerting compression and to provide a simplified and easily manufactured closure system.

SUMMARY OF THE INVENTION

The present invention provides a closure unit for orthoses such as a lumbo-sacral orthosis that permits a first body member conforming to a portion of a patient's torso to be connected through the closure unit, with a second body member conforming to another portion of a patient's torso. The closure system can also be applied to orthoses for other parts of a patient's body in addition to the spine, such as a leg brace, shoulder brace, etc.

The closure unit can be removably attached, for example, by a nap and hook arrangement to be subjectively configured for applying a force having a mechanical advantage. The closure unit includes a first connector member with a first plurality of support posts and a second connector member with a second plurality of support posts with an elongated flexible pull member operatively extending between the respective first and second support posts to provide a mechanical force advantage when tightened by the patient to draw the first body member and the second body member against the patient's torso to exert compression forces. The elongated flexible pull member can comprise a cord such as a nylon cord with an exterior braided configuration. The support posts can comprise rivets that extend between an upper housing member and a lower housing member which can be contained within a fabric housing. In one embodiment, the upper housing member and the lower housing member are relatively flexible plastic plates. A smooth metal sleeve, such as an aluminum or chrome plated steel sleeve, can be fixed about each rivet.

The support posts can be positioned in sets that can overlap a common axis and support plates can be designed to support the support posts so that the support plates can intermesh with each other during assembly.

In an alternative embodiment, a lower housing member can be a bendable metal plate such as an aluminum plate which can be subjectively bent to conform to the configuration of the patient's torso. The lumbo sacral-orthosis can incorporate the closure unit and, if desired, a pair of closure units can be utilized on either side of the orthosis. Thus, the orthosis can have a front torso conforming member and a rear torso conforming member. A first and second closure unit can be positioned to removably interconnect with the respective first body member and the second body member. A fastener member can be connected to the cord of each of the respective closure units with the fastener member including one of a nap or hook material. The other of a nap or hook material can be appropriately positioned, for example, on the front body member, so that a patient who pulls the respective fastener members can removably lock them at a desired compression. As can be appreciated, the front body members can be of a rigid plastic with a soft foam liner or they can be a flexible body member having pockets to receive rigid or semi-rigid inserts and stays. The lumbo-sacral orthosis can be of a modular configuration to permit prefabrication with subsequent selection of modular units to conform the final orthosis for application to the patient.

The method of assembling the closure unit includes positioning a first set of support posts and a second set of support posts so that they overlap a common axis and inserting a pull member along the common axis to extend about each support post on an alternative basis so that when the respective support posts are separated the pull member is operatively threaded between the support posts to provide a mechanical advantage.

BRIEF DESCRIPTION OF THE DRAWINGS

The exact nature of this invention will be readily apparent from consideration of the following detailed description in conjunction with the accompanying drawings, wherein.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein to specifically provide a modular spinal orthosis with an improved pull system to apply compression forces.

Figure 1:
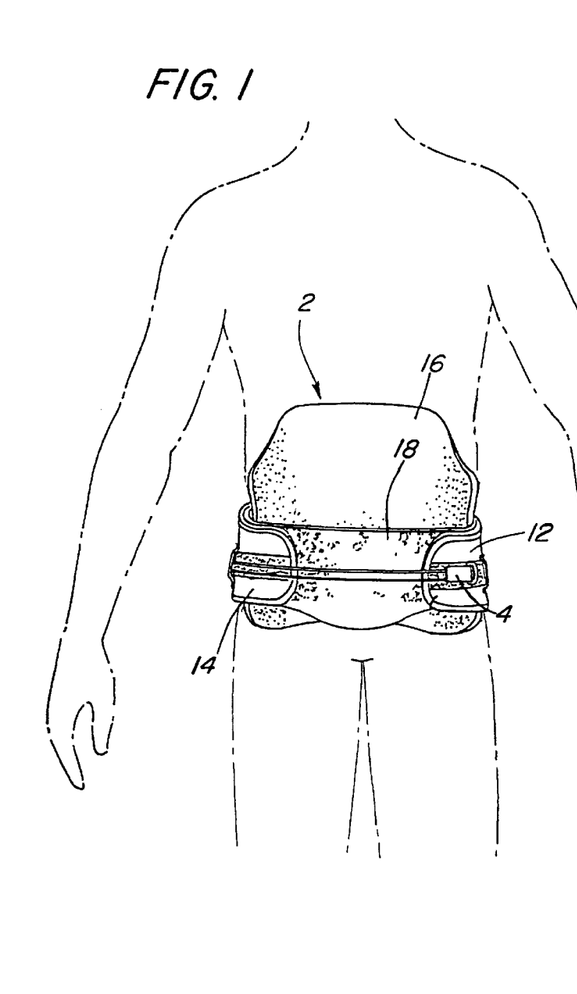
FIG. 1 is a front elevational view of an orthosis of the present invention with one closure unit.
Figure 2:
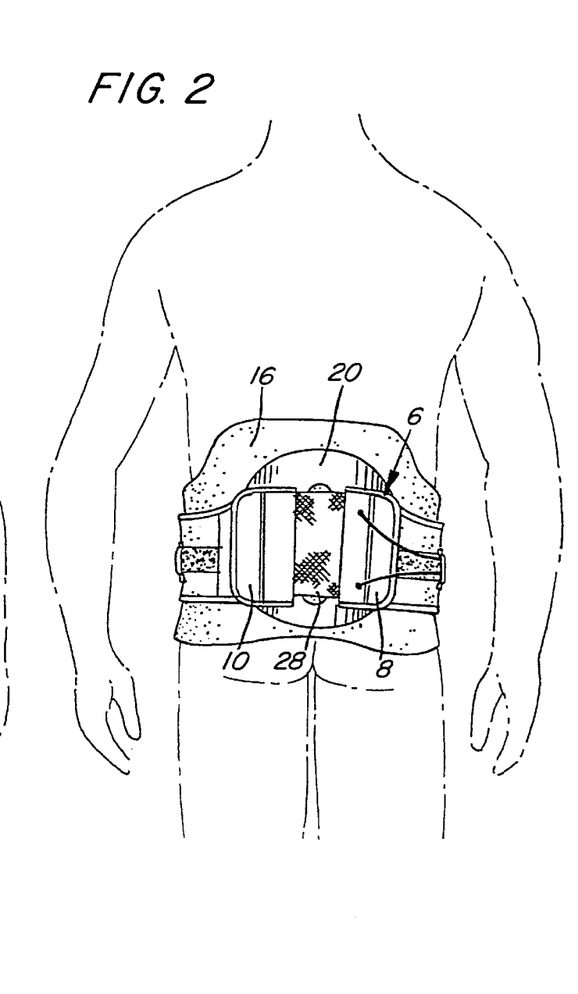
FIG. 2 is a rear elevational view of an orthosis.

A first embodiment of the present invention is disclosed in FIGS. 1 and 2 as a lumbo-sacral orthosis 2 which permits a patient to provide compressive forces about his torso by simply pulling and removably fastening a fastener member 4 to a surface portion of the orthosis. As can be seen in FIG. 2, a closure unit 6 includes a first connector member 8 and a second connector member 10. In the first embodiment, the orthosis can include a first body member 12 conforming to a portion of a patient's torso and a second body member 14 conforming also to another portion of a patient's torso. In this embodiment, the orthosis has basically a belt-like configuration that can complement additional modular components, such as a rear body member 16 and a front body member 18. A semi-rigid plastic support member 20 of an oval configuration can be attached to the exterior of the rear body member 16 as shown in FIG. 2 to provide additional back support. Other configurations of a rigid or semi-rigid rigid support member can be appended to a surface or inserted within a pocket to provide additional support.

Figure 5:
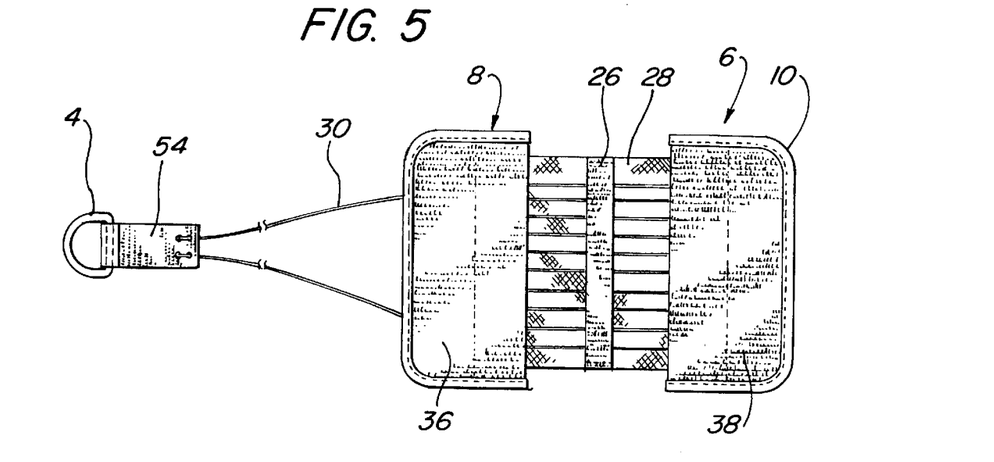
FIG. 5 is a rear elevational view of a closure unit.
Figure 6:
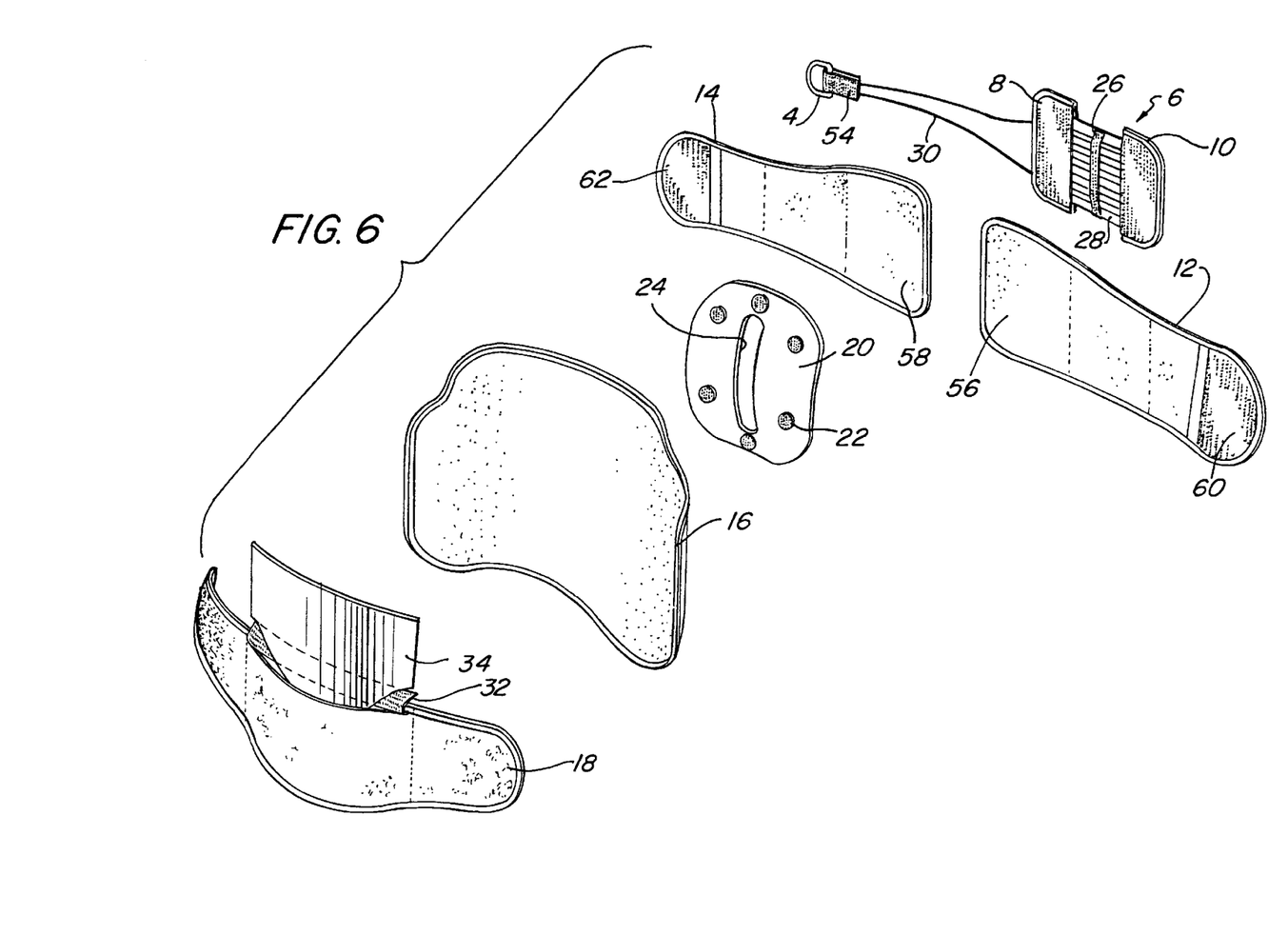
FIG. 6 is an exploded view of a modular lumbo-sacral orthosis.

An exploded view of the first embodiment is shown in FIG. 6. As can be seen, the support member 20 can have a series of patches of a hook-like configuration that is capable of grasping onto the exterior surface of the rear body member 16 which has a nap-like texture. These hook patches 22 can be subjectively positioned both in location and number sufficient to rigidly hold the support member 20 on the rear body member 16. The support member 20 also has a slot 24 centrally located that permits a strip of hook material 26 on the closure unit 6 to extend through the slot 24 and to adhere the closure unit 6 directly to the rear body member 16. An elastic band 28 can be interconnected between the first connector member 8 and the second connector member 10 of the closure unit 6 and can support the hook strip 26 as seen m FIGS. 5 and 6. The hook strip 26 can also capture or encircle the loops of the elongated flexible pull member or cord 30 that extends between the respective first connector member 8 and the second connector member 10 and terminates in the fastener member 4. Thus, the elastic band 28 can assist in aligning the loops of cord between the connector members to stay somewhat in the same place as the elastic band 28 and when mounted, as shown in FIG. 2, covers the exterior side of loops of the cord 30 to prevent snagging on exterior objects. The elastic band 28 can stretch to accommodate relative movement between the first and second connector member when a force is exerted by tightening the elongated flexible pull member. Note, it is possible to provide the closure system without the protective covering of the elastic band, for example, on a compression belt orthosis.

The cord 30 can be formed from a nylon material having an exterior braided surface to thereby provide a low friction, but strong, pull member such as a Dacron cord with a diameter of 0.042 inches and a 90 lb. test strength. As can be appreciated, other arrangements can be provided, such that the rear body member, instead of having an exterior support member 20, can be hollow with a pocket for receiving a plastic stay. The front body member 18 has such a pocket member with a hooked material flap 32 which, when open, can receive a plastic support stay member 34.

Figure 4:
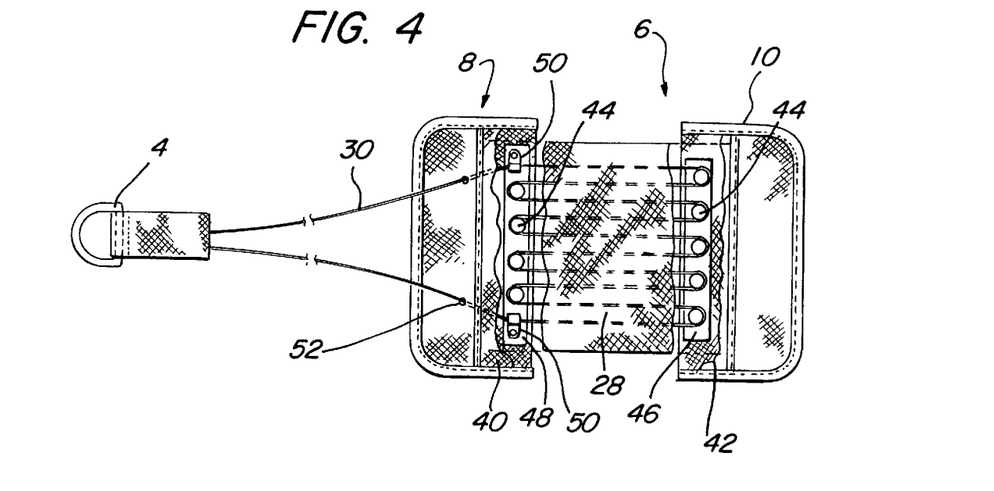
FIG. 4 is a front elevational view of a closure unit.

Referring to FIGS. 4 and 5, the closure unit 6 includes fastener portions on the underside of a hook material 36 on the first connector members 8 and a hook material 38 on the second connector member 10. The upper surface of these connector members is divided into pockets 40 and 42 of webbing that cover and house a plurality of support posts 44 and loop material to which a lower base is sewn. The support posts 44 are respectively affixed to a base member 46. Each of the pockets 40 and 42 have an open slit to permit the cord member to wrap around the respective support posts 44 in each of the connector members to thereby provide a mechanical advantage or force multiplier when the cord 30 is pulled by the patient.

As shown in FIG. 4, a base member 48 in the first connector member 8 can further have pull member guide eyelets 50 that permit the respective ends of the cord member 30 to be aligned so that they can exit through ports 52 for attachment to the fastener member 4. One side of the fastener member 4, as shown in FIG. 5, includes a strip of hook material 54. The rear of the exterior panels 56 and 58 on the respective first body member 12 and body member 14 shown in FIG. 6 can have a nap material, to permit a removable locking of the closure unit 6 in a subjective alignment on the body members to meet the demands of the individual patient. The front internal end portions of the respective first body member 12 and second body member 14 have hook material 60 and 62 that can be used to grasp the nap or loop material on the exterior surface of the front body member 18. Thus, the first body member 12 and the second body member 14 can be adhered to the front body member 18. The closure unit 6 is likewise adhered to the nap material on the rear surface of the first body member 12 and second body member 14 by the hook material 36 and 38. The rear body member 16 can have the plastic support member 20 adhered to its nap exterior surface and the hook strip 26 on the closure unit 6 can then be adhered through the slot 24 to the nap material on the rear body member 16. The user, by pulling upon the fastener member 4 across the front body member 18, can then employ a mechanical advantage to pull the respective first body member 12 and second body member 14 together to provide a compressive force in combination with the front member 18. The fastener member 4 can then be appropriately attached to the nap material on the front of the front body member 18 to maintain the desired compression forces. Fastener member 4 can permit an adjustment for the length of the cord 30 to customize the closure unit 6 to the dimensions of a particular patient.

The ability of the cord 30 to slide with low friction across the respective support posts 44 provides a relatively compact efficient mechanical advantage without requiring additional moving parts such as pulleys. The individual support posts 44 can comprise a rivet assembly having either a sufficiently smooth outer surface, or the body of the rivet can be mounted within a sleeve that is fixed and engaged by a rivet when it is attached to its appropriate base member to extend perpendicularly upward. The nylon cord 30 can appropriately slide across the surface of such a sleeve, for example an anodized aluminum, brass or a steel sleeve coated with chromium. Thus, a relatively economical and compact adjustable lumbo-sacral orthosis with an improved closure unit is provided.

Alternatively, a Teflon™ coating can be applied to the rivet outer surface to directly interface with the pull cord.

It is also possible to use high strength plastic rivets with an outer concave surface to center the pull cord. The base member can also comprise a heavy fabric and the support posts can be custom swagged to lock with the fabric. Alternatively, the support posts can be secured by fasteners such as screws that are axially threaded into threaded apertures in the support posts for fastening onto a base member.

Figures 3, 3A:
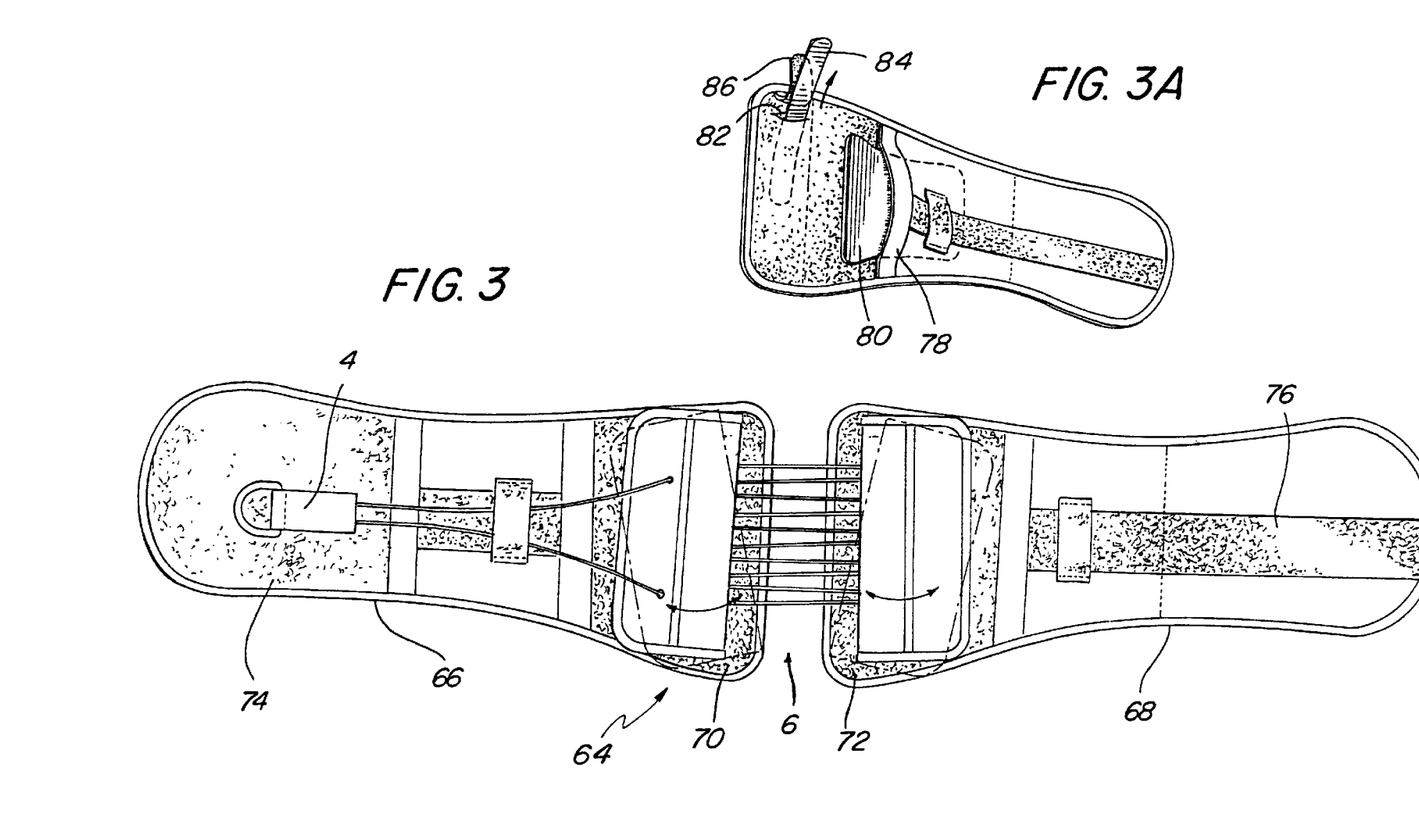
FIG. 3 is a front elevational view of another orthosis of the present invention.
FIG. 3a is a perspective view of a body member of the orthosis of FIG. 3.

Referring to FIGS. 3 and 3*a*, another embodiment of a lumbo-sacral orthosis 64 is disclosed. This orthosis is primarily designed to provide a back support garment and utilizes the closure unit 6 with a first connector member 66 and a second connector member 68. Appropriate nap material 70 and 72 can permit a subjective positioning of the closure unit 6 as shown by the dotted lines and arrows on FIG. 3. An end rear surface, not shown, of the second connector member 68 can have hook material which is capable of attaching to the nap material 74 shown on the front of the first connector member 66. Thus, the respective ends of these connector members can be fastened about the waist of a patient and the fastener member 4 can then be pulled to tighten the closure unit 6 with the fastener member 4 then attached to a strip of nap material 76 on the second connector member 68. To provide additional rigidity, a pocket 78 can be provided on either one or both of the first and second connector members 66 and 68 as shown in FIG. 3*a*. A plastic stay 80 can be inserted into the pocket member to provide an additional support. As can be seen, a second pocket member 82 can receive an elongated stay 84 and can be closed with a tab 86 of a hook material. The particular stays can be made from a plastic material or a relatively bendable metal, e.g., an aluminum plate to thereby permit adjustment to the particular structure of the patient. In this embodiment, a protective elastic cover member is not shown and the cord 30 is exposed. However, an elastic cover member could be used as a protection against any snarling of the loops of cords on exterior objects.

Figure 7:
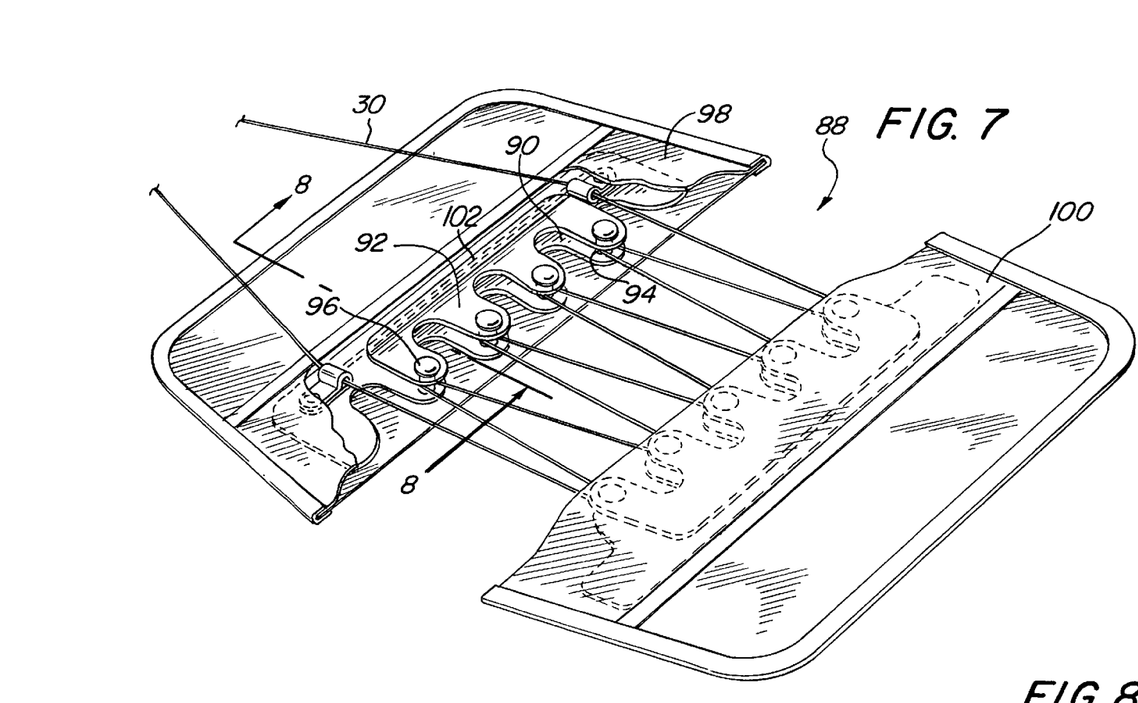
FIG. 7 is a perspective view of a portion of a closure unit.

Referring to FIG. 7, an alternative embodiment of a closure unit is disclosed as closure unit 88. In this embodiment, a pair of semi-rigid plastic plates 90 and 92 are used to sandwich the support posts 94. This arrangement helps to encase the cord 30 to lessen any entanglement of the respective loops. Appropriate rivets can be used to fasten the respective plastic plates 90 and 92 together. As mentioned above, a sleeve member can be used for each support post and can be stationarily fixed by the rivets if desired. It is also possible to stitch or sew the base plastic plate 90 alone or both the base plate 90 and upper plate 92 to the fabric material that forms the respective connector members 98 and 100. The stitching is disclosed on the connector member 98 as element 102 with a 16 oz. thread. The cord 30 is looped between the respective support posts 94 on each of the connector members 98 and 100 and exits through the guide eyelets 50.

Figure 8:
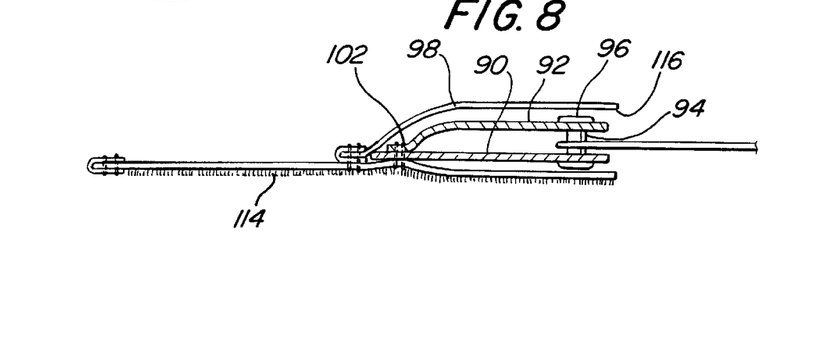
FIG. 8 is a partial cross sectional view along the line 8—8 of FIG. 7.

FIG. 8 is a partial cross sectional view of a connector member with a lower flexible hook member 114 that is fastened to a pocket or flap 116. Both the lower or base plastic plate 90 and the upper plastic plate 92 can be stitched onto the hook member 114. Alternatively, only the plastic plate 90 can be stitched and the upper plastic plate 92 can be cantilevered from the support posts 94.

Figure 9:
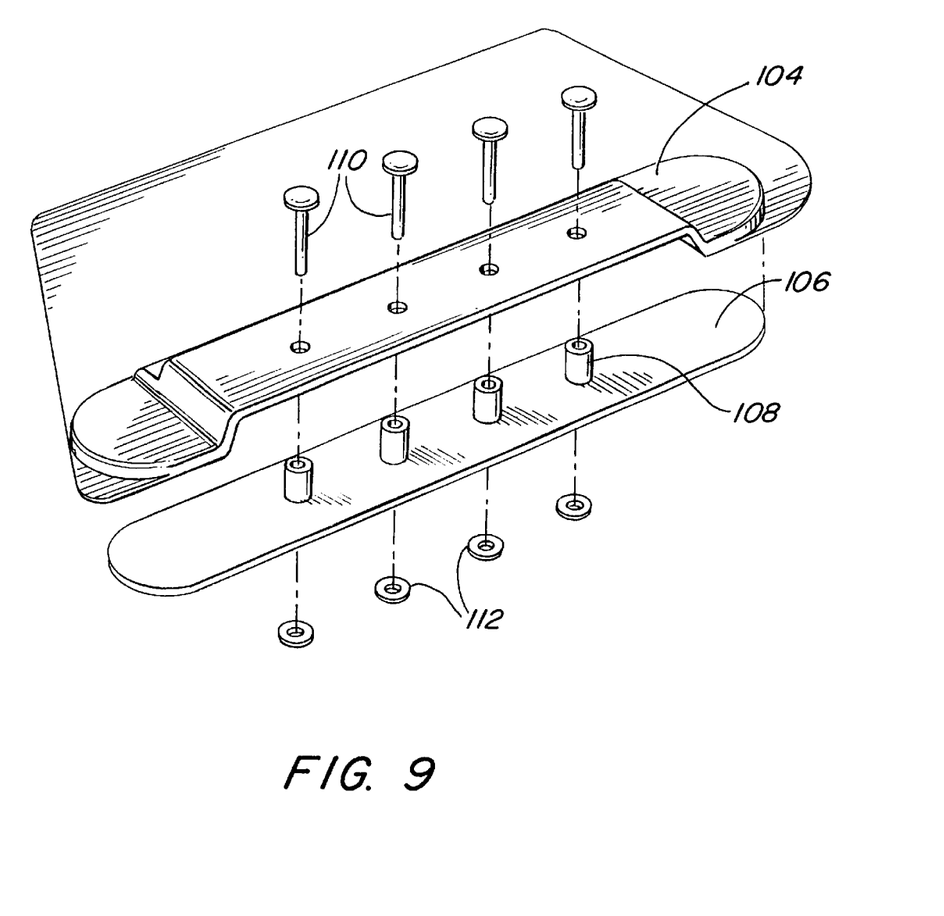
FIG. 9 is a partial exploded view of an alternative component of a closure unit.

An alternative structure for supporting the respective support posts is shown in FIG. 9. In this embodiment, a molded upper plastic housing 104 has a lower cavity that can receive an aluminum plate 106 that is bendable. A plurality of sleeves 108 can again be fastened by appropriate rivets 110 and washers 112 to connect the entire structure together. The use of a bendable metal plate such as an aluminum plate 106 permits a bending of the structure to conform to the desired configuration of the patient. The plastic housing 104 can again be stitched to the fabric covering of the connector member.

Figure 10:
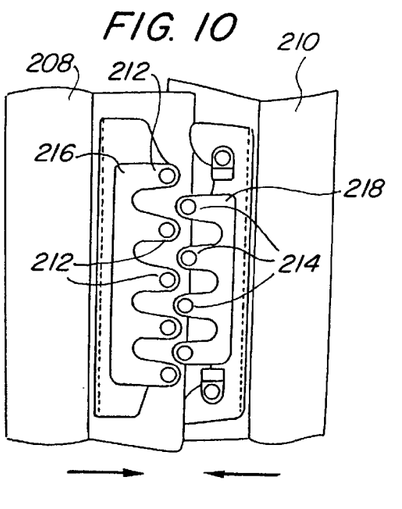
FIG. 10 is a schematic front elevation view of a portion of the closure unit.
Figure 11:
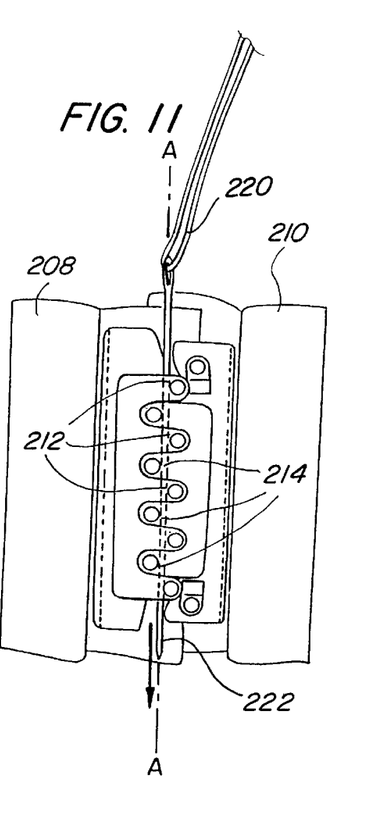
FIG. 11 is a schematic view illustrating a method of manufacturing the closure unit.
Figure 12:
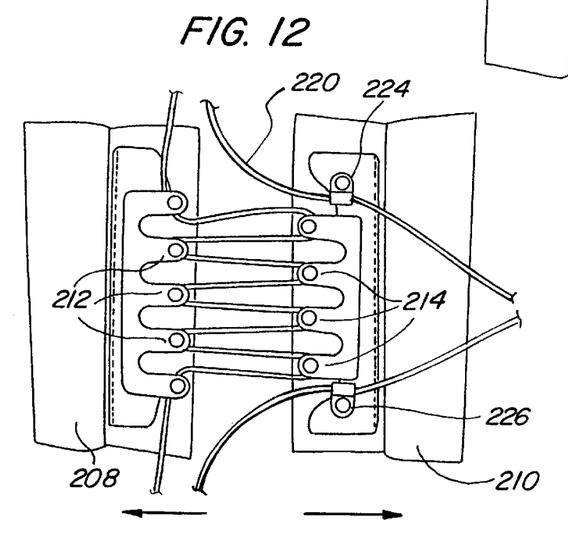
FIG. 12 is a schematic view illustrating the assembly of the pull member.

Referring to FIGS. 10, 11 and 12, an efficient and economical method of assembling the closure system of the present invention is disclosed. A first connector member 208 and a second connector member 210 position their respective support posts 212 and 214 in an aligned linear arrangement. Additionally, the respective base plates (not shown) and upper plates 216 and 218 are appropriately notched or indented to provide undulating surfaces that are offset so that when they are placed together, as shown in FIG. 11, they interlock and provide a straight pathway along a common central axis A—A for receiving a pull cord 220 that can be inserted with a mechanical instrument such as an elongated needle 222. Thus, the appropriate design of the upper and lower plates not only provides a guide for the pull cord 220 when in operation, but is further designed to facilitate the assembly of the closure unit by permitting the support posts 212 to overlap the corresponding support posts 214 for receiving the insertion needle 222. Thus, any tedious labor intensive procedure of threading the pull cord 220 through the respective support posts can be eliminated through the unique design of cantilevering each set of the support posts to permit an intermeshing and overlapping of the support posts as shown in FIG. 11. When the connector members 208 and 210 are then pulled apart, the cord 220 is appropriately positioned and then can be threaded through the guides 224 and 226.

In each of the above embodiments, the different positions and structures of the present invention are described separately in each of the embodiments. However, it is the full intention of the inventors of the present invention that the separate aspects of each embodiment described herein may be alternatively combined with the other embodiments described herein to provide hybrid embodiments to meet the requirements of each patient.

Those skilled in the art will appreciate that adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A modular orthosis for the progressive treatment of a patient, comprising:
   a first orthosis having a front body member conforming to a portion of a patient's torso, and a rear body member conforming to another portion of a patient's torso, the rear and front body members are operatively positioned to provide relative movement for compression of the patient's torso pursuant to a first course of treatment; and
   a second orthosis having a first body member, with nap texture on an exterior of one end, the first body member with nap texture is flexible with a pocket to receive a relatively rigid insert, a second body member with nap texture on an exterior of one end, the second body member with nap texture is flexible with a pocket to receive a relatively rigid insert, and a closure unit with a first connector member having a size smaller than the respective nap texture sizes with hook texture on one surface and a second connector member having a size smaller than the respective nap texture sizes with hook texture on one surface, the first connector member is removably and adjustably fastened by interaction of the first body member nap texture with the first connector member hook texture to permit a two-dimensional adjustment location of the first connector member on the first body member to subjectively fit the patient and the second connector member is removably and adjustably fastened by interaction of the second body member nap texture with the second connector member hook texture to permit a two-dimensional adjustment location of the second connector member on the second body member to subjectively fit the patient, the second orthosis is removably connected to an exterior of the first orthosis whereby the closure unit can exert a force to provide relative movement of the front and rear body members during the first course of treatment, the second orthosis is dimensioned to conform to the patient's body when removed from the first orthosis whereby the first body member and the second body member can be directly positioned about the patient's body and the closure unit can exert a compressive force through the first body member and the second body member to the patient's body to provide a second course of treatment; wherin the first connector member has a first plurality of support posts, a second connector member has a second plurality of support posts operatively connected to the second body member, and an elongated flexible pull member operatively extending between the respective first and second support posts to provide a mechanical advantage when tightened by the patient to draw the first body member and second body member against the patient's torso to provide compression of the patient's torso.

2. The modular orthosis of claim 1 wherein the support posts are plastic.

3. The modular orthosis of claim 1 wherein the first connector member includes an upper housing member and a lower housing member operatively connected together and interconnected by the plurality of support posts.

4. The modular orthosis of claim 3 wherein the upper housing member and the lower housing member are relatively flexible plastic plates.

5. The modular orthosis of claim 4 further including at least one pull member guide.

6. The modular orthosis of claim 3 wherein the lower housing member is a bendable metal plate.

7. The modular orthosis of claim 3 wherein the plurality of support posts are rivets.

8. The modular orthosis of claim 7 wherein a chrome plated steel sleeve is fixed to each rivet.

9. The modular orthosis of claim 3 wherein the elongated flexible pull member is a cord.

10. The modular orthosis of claim 9 further including a fastener member connected to both ends of the cord for attachment to one of the first and second body members.

11. The modular orthosis of claim 3 wherein the elongated flexible pull member is a braided nylon cord.

12. The modular orthosis of claim 1 wherein the configuration of the first connector member and the second connector member is complimentary to enable their respective support posts to overlap a common axis.

13. The modular orthosis of claim 12 wherein the respective first and second connector members have intermeshing surfaces when overlapping the common axis.

14. The modular orthosis of claim 13 where the intermeshing surfaces have an undulating appearance.

15. The modular orthosis of claim 12 wherein the first and second plurality of support posts have axes extending approximately perpendicular to the surface of the second body member.

16. The modular orthosis of claim 1 further including an elastic band member interconnected between the first and second connector members to cover an exterior side of the flexible pull member.

17. The modular orthosis of claim 16 further including a hook material on the elastic band member to adhere the elastic band member to the rear body member.

18. The modular orthosis of claim 16 wherein the rear body member has a plastic housing with a soft foam liner.

19. The modular orthosis of claim 1 wherein the front body member has a plastic housing with a soft foam liner.

20. The modular orthosis of claim 1 wherein the front body member has an exterior with a nap material to enable a removable connection with the first body member and the second body member.

21. A lumbo-sacral orthosis comprising:
a first orthotic assembly having a first front body member conforming to a portion a patient's torso;
a second back body member conforming to a portion of a patient's torso, the combination of the first front member and second back member providing a first orthotic for stabilizing a patient's torso, the first front member includes a flexible body member having a pocket to receive a relatively rigid insert, an exterior of the pocket has a nap surface texture; and
a closure unit for providing a mechanical advantage to exert a compressive force on the patient's torso by drawing the first front body member and second back body member together, the closure unit includes a first body member and a second body member of a configuration to extend about at least a portion of the first front body member and the second back body member, the first body member has a first pocket member to receive a first stay member and the second body member has a second pocket member to receive a second stay member, a first connector member having a first support housing with a first plurality of support posts that can be operatively connected to the first body member, the first plurality of support posts are fixed and have axes which would extend approximately perpendicular to the surface of the patient and are spaced and aligned to be respectively cantilevered, a second connector member having a second support housing with a second plurality of support posts that can be operatively connected to the second body member, the second plurality of support posts are fixed and have axes which would extend approximately perpendicular to the surface of the patient and are spaced and aligned to be respectively cantilevered, the first and second connector members include surfaces of a hook texture, and the first body member and second body member include surfaces of a nap texture to provide an adjustable fastening attachment with the hook texture surfaces of the first and second connector members, the first body member and the second body member include hook texture surfaces for removably engaging the first front member nap surface, and an elongated flexible pull member operatively extending for sliding movement directly between the respective first and second support posts to provide a mechanical force advantage when tightened by the patient to draw the first body member and second body member to exert a compressive force against the patient's body, the closure unit providing a second orthotic assembly for exerting a compressive force through the first body member and second body member when removed from the first orthotic assembly.

22. The lumbo-sacral orthosis of claim 21, whereby the respective axes are juxtapositioned to be movable so that the first plurality of support posts can be placed on one side of the second plurality of support posts during assembly to receive the elongated flexible pull member and placed on another side of the second plurality of support posts during operation to provide a mechanical force advantage.

23. The lumbo-sacral orthosis of claim 22 wherein the first and second stay members are formed of an elongated bendable aluminum configuration.

24. The lumbo-sacral orthosis of claim 22 wherein the first support housing includes an upper plastic member and a lower plastic member operatively connected together and interconnected by a plurality of plastic support posts.

* * * * *